United States Patent
Chen et al.

(10) Patent No.: US 12,245,818 B2
(45) Date of Patent: Mar. 11, 2025

(54) APPARATUS AND METHOD FOR ASSISTING PUNCTURE PLANNING

(71) Applicant: KONINKLIJKE PHILIPS N.V., Eindhoven (NL)

(72) Inventors: Yinan Chen, Shanghai (CN); Fan Li, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 868 days.

(21) Appl. No.: 16/958,077

(22) PCT Filed: Dec. 20, 2018

(86) PCT No.: PCT/EP2018/086054
§ 371 (c)(1),
(2) Date: Jun. 25, 2020

(87) PCT Pub. No.: WO2019/129606
PCT Pub. Date: Jul. 4, 2019

(65) Prior Publication Data
US 2020/0315710 A1   Oct. 8, 2020

(30) Foreign Application Priority Data

Dec. 28, 2017  (WO) ................ PCT/CN2017/119450
Apr. 11, 2018  (EP) .................................... 18166743

(51) Int. Cl.
*A61B 34/10*      (2016.01)
*G16H 10/60*      (2018.01)
(Continued)

(52) U.S. Cl.
CPC ............ *A61B 34/10* (2016.02); *G16H 10/60* (2018.01); *G16H 20/40* (2018.01); *G16H 30/40* (2018.01);
(Continued)

(58) Field of Classification Search
CPC ... A61B 2034/107; A61B 34/20; A61B 34/10; G16H 20/40; G16H 50/50; G16H 40/60
See application file for complete search history.

(56) References Cited

U.S. PATENT DOCUMENTS

2009/0198124 A1   8/2009  Adamus et al.
2009/0259230 A1  10/2009  Khadem et al.
(Continued)

FOREIGN PATENT DOCUMENTS

WO         9942977 A1    8/1999
WO   WO-2006027781 A2 *  3/2006  ............. A61B 34/20
(Continued)

OTHER PUBLICATIONS

Tsauo, Jiaywei, et al. "Three-dimensional path planning software-assisted transjugular intrahepatic portosystemic shunt: a technical modification." Cardiovascular and interventional radiology 38.3 (2015): 742-746. (Year: 2015).*

(Continued)

*Primary Examiner* — Jason B Dunham
*Assistant Examiner* — Constantine Siozopoulos

(57) ABSTRACT

The present invention proposes an apparatus and method for assisting a user to plan a puncture trajectory within a region-of-interest of a subject. The apparatus comprises: a data interface (211) configured to receive anatomical data of the region-of-interest of the subject and to output the at least one candidate puncture trajectory, and a data processor (213) for calculating at least one candidate puncture trajectory on basis of the anatomical data, multiple criteria, and a tradeoff among the multiple criteria. The anatomical data of the subject comprises three-dimensional data of the region of interest. The data processor (213) is further configured, upon receiving a first user input for adjusting the tradeoff among the multiple criteria, to adjust the tradeoff among the multiple criteria on basis of the first user input, and to calculate the at least one candidate puncture trajectory on basis of the anatomical data, the multiple criteria and the adjusted tradeoff among the multiple criteria. Different from conventional automatic planning tools which tend to offer a universal best tradeoff among multiple criteria for all cases, the proposed apparatus allows the user to tailor the tradeoff and thus tailor the automatic calculation of the candidate puncture trajectories so as to better meet the actual clinical needs.

15 Claims, 9 Drawing Sheets

(51) Int. Cl.
   *G16H 20/40* (2018.01)
   *G16H 30/40* (2018.01)
   *G16H 50/20* (2018.01)
   *A61B 90/00* (2016.01)

(52) U.S. Cl.
   CPC ........ *G16H 50/20* (2018.01); *A61B 2034/107* (2016.02); *A61B 2090/367* (2016.02); *A61B 2090/378* (2016.02)

(56) References Cited

U.S. PATENT DOCUMENTS

| | | | |
|---|---|---|---|
| 2010/0217117 A1* | 8/2010 | Glossop | A61B 34/20 600/424 |
| 2013/0085344 A1 | 4/2013 | Merkl et al. | |
| 2017/0049511 A1 | 2/2017 | Uhm et al. | |
| 2018/0228554 A1* | 8/2018 | Strommer | A61B 6/504 |

FOREIGN PATENT DOCUMENTS

| | | |
|---|---|---|
| WO | 2014019714 A2 | 2/2014 |
| WO | 2016083927 A1 | 6/2016 |
| WO | 2016181317 A2 | 11/2016 |

OTHER PUBLICATIONS

PCT/EP2018/086054 ISR & WO, Apr. 4, 2019, 14 Page Document.

Andring et al: "Effect of Technical Parameters on Transjugular Intrahepatic Portosystemic Shunts Utliizing Stent Grafts"; World Journal of Gastroenterology, Jul. 2015, pp. 8110-8117.

Bourquain et al: "Hepavision2—A Software Assistant for Preoperative Planning in Living-Related Liver Transplantation and Oncologic Liver Surgery"; CARS 2002, Computer Assisted Radiology and Surgery, pp. 341-346.

Cuijpers et al: "Real-Time Three-Dimensional Ultrasound User Interface for Tips Planning"; European Society of Radiology (ECR) 2015, 6 Page Document.

Farsad et al: "Novel Image Guidance Techniques for Portal Vein Targeting During 5 Transjulular Intrahepatic Portosystemic Shunt Creation"; Techniques in Vascular and Interventional Radiology, Elseivier Inc, 2016 pp. 10-20.

* cited by examiner

APPARATUS AND METHOD FOR ASSISTING PUNCTURE PLANNING

CROSS-REFERENCE TO PRIOR APPLICATIONS

This application is the U.S. National Phase application under 35 U.S.C. § 371 of International Application No. PCT/EP2018/086054, filed on Dec. 20, 2018, which claims the benefit of European Patent Application No. 18166743.7, filed on Apr. 11, 2018 and CN Patent Application No. PCT/CN2017/119450, filed Dec. 28, 2017. These applications are hereby incorporated by reference herein.

FIELD OF THE INVENTION

The present invention relates to puncture planning, and more particularly to an apparatus and method for assisting a user to plan a puncture trajectory between, for example, two vessels of a subject.

BACKGROUND OF THE INVENTION

Portal hypertension, an important consequence of chronic liver disease, results in the development of significant collateral circulation between the portal system and systemic venous drainage. Portal venous congestion causes venous blood leaving the stomach and intestines to be diverted along auxiliary routes of lesser resistance in order to drain to systemic circulation. With time, the small vessels that comprise a collateral path for porta-caval circulation become engorged and dilated. These vessels are fragile and often hemorrhage into the gastrointestinal tract. A Trans jugular Intra-hepatic Portosystemic Shunt (TIPS) procedure decreases the effective vascular resistance of the liver through the creation of an alternative pathway for portal venous circulation. A shunt is used to establish an artificial channel between the inflow portal vein (PV) and the outflow hepatic vein (HV). It regards as a palliative treatment for portal hypertension which frequently leads to intestinal bleeding, life-threatening esophageal bleeding and the buildup of fluid within the abdomen (i.e. ascites).

TIPS is typically performed by an interventional radiologist under fluoroscopic guidance. Access to the liver is gained, as the name 'transjugular' suggests, via the internal jugular vein in the neck. Once access to the jugular vein is confirmed, a guidewire and introducer sheath are typically placed to facilitate the shunt's placement. This enables the interventional radiologist (IR) to gain access to the patient's hepatic vein by travelling from the superior vena vava into the inferior vena cava (IVC) and finally the hepatic vein. From the IVC, IR inserts the catheter in a branch of the HV. A special needle is advanced through the liver parenchyma to connect the hepatic vein to the large PV. The channel for shunt is next created by inflating an angioplasty balloon within the liver along the tract created by needle. The shunt is completed by placing a special mesh tube known as a stent or endograft to maintain the tract between the higher-pressure portal vein and the lower-pressure hepatic vein. The shunt allows a decompression of portal hypertension, since PV blood is now diverted into the systemic circulation.

FIG. 1 schematically illustrates a puncture trajectory (also called a puncture track) in TIPS procedure. There are many HV branches and PV branches. FIG. 1 illustrates 3 HV branches 120-1, 120-2 and 120-3, and 2 PV branches 130-1, 130-2, but in clinical case either of the number of HV branches and the number of PV branches is random and can be any number of branches. FIG. 1 illustrates a puncture trajectory 140 which starts from the exit point 141 on the HV branch 120-1, advances through the liver parenchyma 110, and arrives at the entry point 142 on the PV branch 130-1. Theoretically, a puncture tract between any point on any PV branch and any point on any HV branch can work as an alternative pathway for portal venous circulation, and thus there are many possible puncture tracts to build the connection between HV and PV. In practice, the choice of tracts will result in multiple impacts on clinical outcome, and choosing a most desirable puncture trajectory is a quite challenging task for IRs.

US 2010/217117 A1 discloses systems and methods for assisting/performing image-guided transjugular intrahepatic portosystemic shunt (TIPS) procedure. It focus on guiding the puncture needle to the target portal vein by tracking the tip position and orientation of the puncture needle. It does not mention how to plan a puncture trajectory at all.

SUMMARY OF THE INVENTION

Therefore, it would be advantageous to provide a technical solution for assisting the planning of a puncture trajectory. Puncture trajectory is also called puncture track, and both terms are used interchangeably herein.

In accordance with an embodiment of a first aspect of the present invention, there is provided an apparatus for assisting a user to plan a puncture trajectory between a portal vein and a hepatic vein of a subject. The apparatus comprises a data interface configured to receive anatomical data of the subject, and a data processor configured to calculate at least one candidate puncture trajectory based on the anatomical data, multiple criteria, and a tradeoff among the multiple criteria. The anatomical data of the subject comprises three-dimensional data of at least one portal vein and at least one hepatic vein of the subject. The multiple criteria comprises spatial distance of the puncture trajectory), and at least one of the following: (a) spatial distance between bifurcation of main branch of portal vein and the puncture point on the portal vein, (b) steepness of the puncture trajectory with respect to the transverse plane of the subject, and (c) Puncture slice distance ($Z_{H\text{-}P}$) along the longitudinal direction (z) of the subject.

The spatial distance of the puncture trajectory is regarded as a significant factor to predict the one-year shunt patency and the risk of HEP occurrence. The smaller value of the spatial distance of the puncture trajectory, the lower risk of shunt occlusion and HEP. The inventors of the present invention have recognized that in addition to the spatial distance of the puncture trajectory, any of the other three factors can play important roles in planning the puncture trajectory. The multiple criteria generally conflict with each other, and thus have to be balanced, or in other words, the trade-off among multiple criteria has to be made. Impacts of the various criteria or factors can be different among different subjects and/or different IRs. By allowing the tradeoff between the spatial distance of the puncture trajectory as well as any of the other factors, the multiple criteria can be balanced with each other, the proposed apparatus enables assistance in planning the puncture trajectory that is more flexible and controllable.

The inventors of the present invention have observed that the choice of puncture tracts will result in multiple impacts on clinical outcome, the IRs, when choosing a most desirable puncture tract, normally need to consider multiple clinical metrics which may be mutually interfered, and the IRs may have to make tradeoff among the clinical metrics. Moreover, the inventors have recognized that details of anatomical structures, such as the structures of HV branches and PV branches, of one subject may be different from another subject, the desirable choice for a particular subject by one IR may be different from another IR depending on IRs skills, experience and preference, and the desirable choice may also depends on the physical conditions of a particular subject.

In some embodiments, the data processor is further configured, upon receiving a first user input for adjusting the tradeoff among the multiple criteria, to adjust the tradeoff among the multiple criteria on basis of the first user input, and to calculate the at least one candidate puncture trajectory on basis of the anatomical data, the multiple criteria and the adjusted tradeoff among the multiple criteria, and the data interface is further configured to output the at least one candidate puncture trajectory.

In accordance with a further embodiment of the first aspect of the present invention, there is proposed an apparatus for assisting a user to plan a puncture trajectory within a region-of-interest of a subject. The apparatus comprises: a data interface configured to receive anatomical data of the region-of-interest of the subject and to output the at least one candidate puncture trajectory, and a data processor for calculating at least one candidate puncture trajectory on basis of the anatomical data, multiple criteria, and a tradeoff among the multiple criteria. The anatomical data of the subject comprises three-dimensional data of the region of interest. The data processor is further configured, upon receiving a first user input for adjusting the tradeoff among the multiple criteria, to adjust the tradeoff among the multiple criteria on basis of the first user input, and to calculate the at least one candidate puncture trajectory on basis of the anatomical data, the multiple criteria and the adjusted tradeoff among the multiple criteria. In some embodiments, the puncture trajectory is between two vessels. The multiple criteria can comprise clinical metrics or non-clinical metrics.

By the use of an adjustable tradeoff among the multiple criteria, the apparatus can not only automatically provide one or more candidate puncture trajectories which meet the multiple criteria in a better way among all possibilities, but also allows the user to adjust the tradeoff among the multiple criteria as needed so as to be able to, for example, more favor one criterion in one case and more favor another criterion in another case depending on users' choices. Different from conventional automatic planning tools which tend to offer a universal best tradeoff among multiple criteria for all cases, the proposed apparatus allows the user to tailor the tradeoff and thus tailor the automatic calculation of the candidate puncture trajectories so as to better meet the actual clinical needs, as recognized by the inventors.

In some embodiments, the data processor is further configured to calculate at least one candidate puncture trajectory on basis of the anatomical data, the multiple criteria, and a predetermined tradeoff among the multiple criteria, and the predetermined tradeoff represents an extreme choice of the tradeoff among the multiple criteria.

The calculation of candidate puncture trajectory by considering multiple criteria and the tradeoff among them belongs to Multiple-criteria decision making (MCDM) problems. Typically, the tradeoff among the multiple criteria is hard to set, because the relationship among the multiple criteria as well as the impact of the tradeoff on the result are normally not straightforward and hard to be predicted. Hence, it would be quite challenging for the user, especially inexperienced users, to adjust the tradeoff although such flexibility is desirable. The at least one candidate puncture trajectory calculated on basis of some extreme choices of the tradeoff among the multiple criteria represent the corresponding boundary cases for a particular subject, and such boundary cases can help the users tune or adjust the tradeoff for that particular subject. In other words, the inventors have proposed a very unique strategy, firstly to present the user with the boundary cases of different criteria, and then to allow the users to fine tune the candidate puncture tracts by adjustment of the tradeoff among the different criteria depending on their judgement.

In accordance with some embodiments, the proposed apparatus further comprises a user interface configured to receive the first user input and to present the at least one candidate puncture trajectory. Additionally and alternatively, the proposed apparatus can be communicatively connected to a user interface configured to receive the first user input and to present the at least one candidate puncture trajectory, and the data interface of the proposed apparatus is configured to communicate with the user interface.

In some embodiments, the user interface is further configured to present the at least one candidate puncture trajectory along with the associated tradeoff among the multiple criteria. In some other embodiments, the data processor is further configured to generate an image of the region-of-interest overlaid with the at least one candidate puncture trajectory.

In accordance with some embodiments, the tradeoff among the multiple criteria is represented by at least one weight, each weight is associated with one of the multiple criteria. In some embodiments, provided with the at least one weight, the multiple criteria can be transformed into a single criterion by multiplying each criterion with the associated weight and summing up the weighted criteria. In this way, it allows the user to adjust the at least weight to tailor the calculation of the candidate puncture trajectories. The apparatus can be configured in such a way that some of the criteria are associated with a predetermined, fixed weight whilst others are associated with the at least one weight which can be adjusted by the users.

In accordance with some embodiments, the data processor is further configured to store historical data, wherein the historical data comprises the calculated at least one candidate puncture trajectory associated with each first user input received, and the data processor is further configured to retrieve, upon a second user input for selecting one received first user input, the at least one candidate puncture trajectory associated with the selected first user input from the stored historical data. In this way, it allows the user to review the former user inputs on the tradeoff and the associated candidate puncture trajectories.

In accordance with some embodiments, the data process is further configured to calculate, for each of at least one of the multiple criteria, an objective value achieved by one of the at least one candidate puncture trajectory, and the data interface is configured to output the calculated objective value(s). The objective value(s) can allow the user to quantitatively assess how the at least one candidate puncture trajectory meets the multiple criteria.

In accordance with some embodiments, the anatomical data comprises three-dimensional ultrasound data of anatomical structures in the region-of-interest. Additionally and alternatively, the anatomical data can comprise three-dimensional data of other imaging modalities, such as MR, CT, x-ray etc.

In accordance with some embodiments, the puncture trajectory is between two vessels, such as a portal vein and a hepatic vein in the region-of-interest of the subject, and the anatomical data comprises anatomical data of the two vessels, such as anatomical data of at least one portal vein branch and at least one hepatic vein branch. Additionally and alternatively, the puncture can be performed in other areas, such as gastrointestinal tract.

In some embodiments, the predetermined multiple criteria comprises (1) spatial distance of the puncture trajectory $D_{H\text{-}P}$ and (2) at least one of the following: (a) spatial distance between bifurcation of main branch of portal vein and the puncture point on the portal vein $D_{P\text{-}B}$, (b) steepness $\theta_{x\text{-}y}$ of the puncture trajectory with respect to the transverse plane (i.e. the x-y plane) of the subject, and (c) puncture slice distance $Z_{H\text{-}P}$ along the longitudinal direction z of the subject.

In accordance with an embodiment of a second aspect of the present invention, there is proposed a method of assisting a user to plan a puncture trajectory between a portal vein and a hepatic vein of a subject. The computer-implemented method comprises: receiving, via a data interface, anatomical data of the subject; calculating, via a data processor, at least one candidate puncture trajectory on basis of the anatomical data, multiple criteria, and a tradeoff among the multiple criteria; and outputting, via the data interface, the at least one candidate puncture trajectory associated with the adjusted tradeoff. The anatomical data of the subject comprises three-dimensional data of at least one portal vein and at least one hepatic vein of the subject. The multiple criteria comprises: spatial distance of the puncture trajectory ($D_{H\text{-}P}$); and at least one of the following: (a) Spatial distance between bifurcation of main branch of portal vein and the puncture point on the portal vein ($D_{P\text{-}B}$); (b) Steepness ($\theta_{x\text{-}y}$) of the puncture trajectory with respect to the transverse plane (x-y) of the subject; and (c) Puncture slice distance ($Z_{H\text{-}P}$) along the longitudinal direction (z) of the subject.

In some embodiments, the computer-implemented method further comprises: receiving a first user input for adjusting the tradeoff among multiple criteria; and adjusting the tradeoff among the multiple criteria on basis of the first user input. The at least one candidate puncture trajectory is calculated on basis of the anatomical data, multiple criteria, and the adjusted tradeoff among the multiple criteria.

In accordance with a further embodiment of the second aspect of the present invention, there is proposed a method of assisting a user to plan a puncture trajectory between within a region-of-interest of a subject. The method comprises: receiving anatomical data of the subject, the anatomical data of the region-of-interest comprising three-dimensional data of the region-of-interest; receiving a first user input for adjusting the tradeoff among multiple criteria; adjusting the tradeoff among the multiple criteria on basis of the first user input; calculating at least one candidate puncture trajectory on basis of the anatomical data, the multiple criteria, and the adjusted tradeoff among the multiple criteria; and outputting the at least one candidate puncture trajectory associated with the adjusted tradeoff.

In accordance with some embodiments, the proposed method further comprises: prior to receive the first user input, calculating at least one candidate puncture trajectory on basis of the anatomical data, the multiple criteria, and a predetermined tradeoff among the multiple criteria; and outputting the at least one candidate puncture trajectory associated with the predetermined tradeoff. In some embodiments, the predetermined tradeoff represents an extreme choice of the tradeoff among the multiple criteria.

In accordance with an embodiment of a third aspect of the present invention, there is proposed a computer-readable medium comprising executable instructions, which when executed, cause a processor to perform any of the proposed methods.

Other objects and advantages of the present invention will become more apparent and can be easily understood with reference to the description made in combination with the accompanying drawings.

SHORT DESCRIPTION OF THE DRAWINGS

The present invention will be described and explained hereinafter in more detail in combination with embodiments and with reference to the drawings, wherein:

FIG. 1 schematically illustrates a puncture trajectory in TIPS procedure;

FIG. 2 schematically illustrates an apparatus for assisting a user to plan a puncture trajectory within a region-of-interest of a subject in accordance with some embodiments of the present invention;

FIG. 3 schematically illustrates a method of assisting a user to plan a puncture trajectory within a region-of-interest of a subject in accordance with some embodiments of the present invention;

FIG. 4 schematically illustrates an exemplary view presented by a user interface in accordance with some embodiments of the present invention;

FIG. 5 schematically illustrates exemplary multiple criteria for planning a puncture trajectory for a TIPS procedure in accordance with some embodiments of the present invention;

Figure 7A:
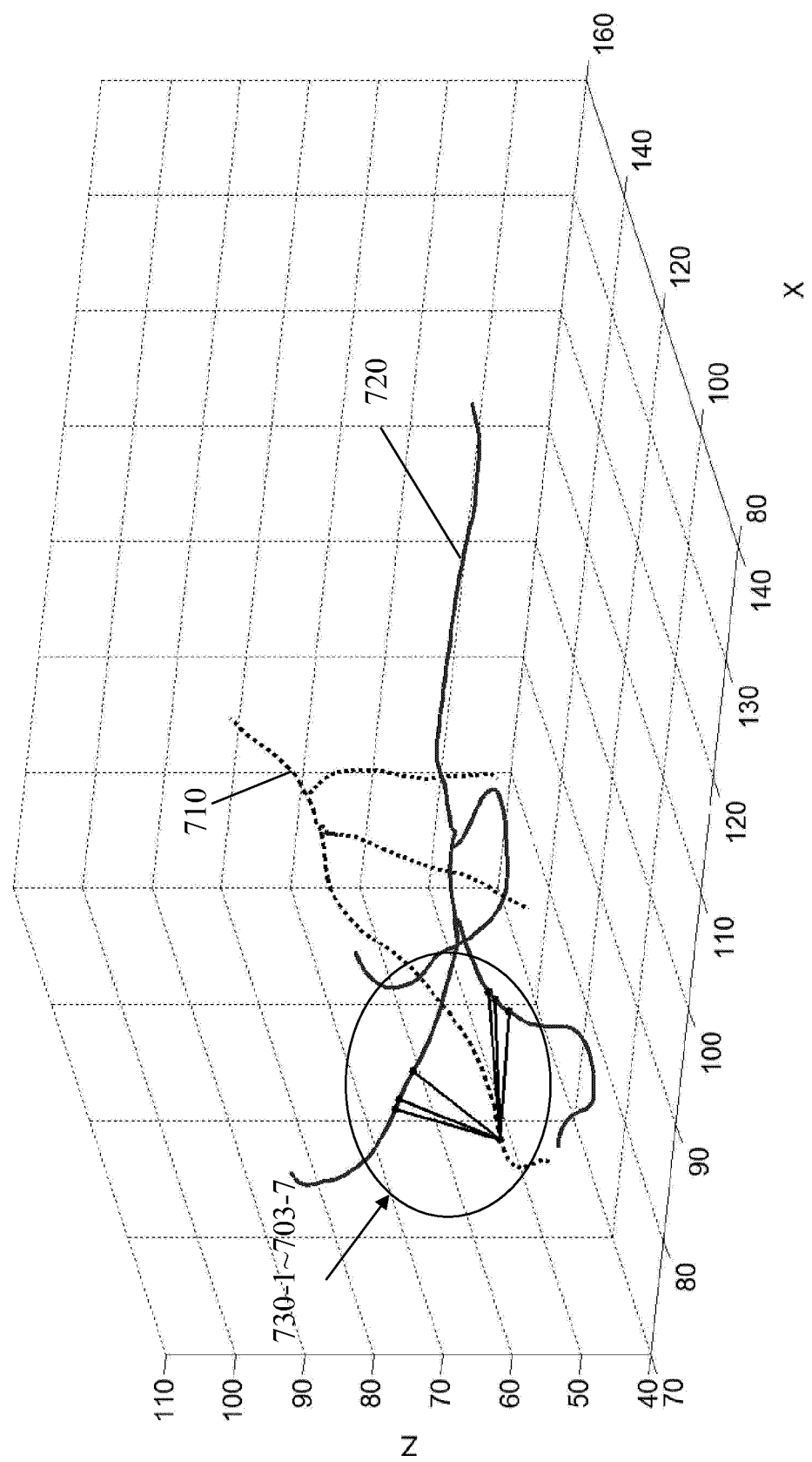
FIG. 7a illustrates a three-dimensional view of several candidate puncture trajectories overlaid with the HV branches and PV branches in accordance with an embodiment of the present invention.
Figure 7B:
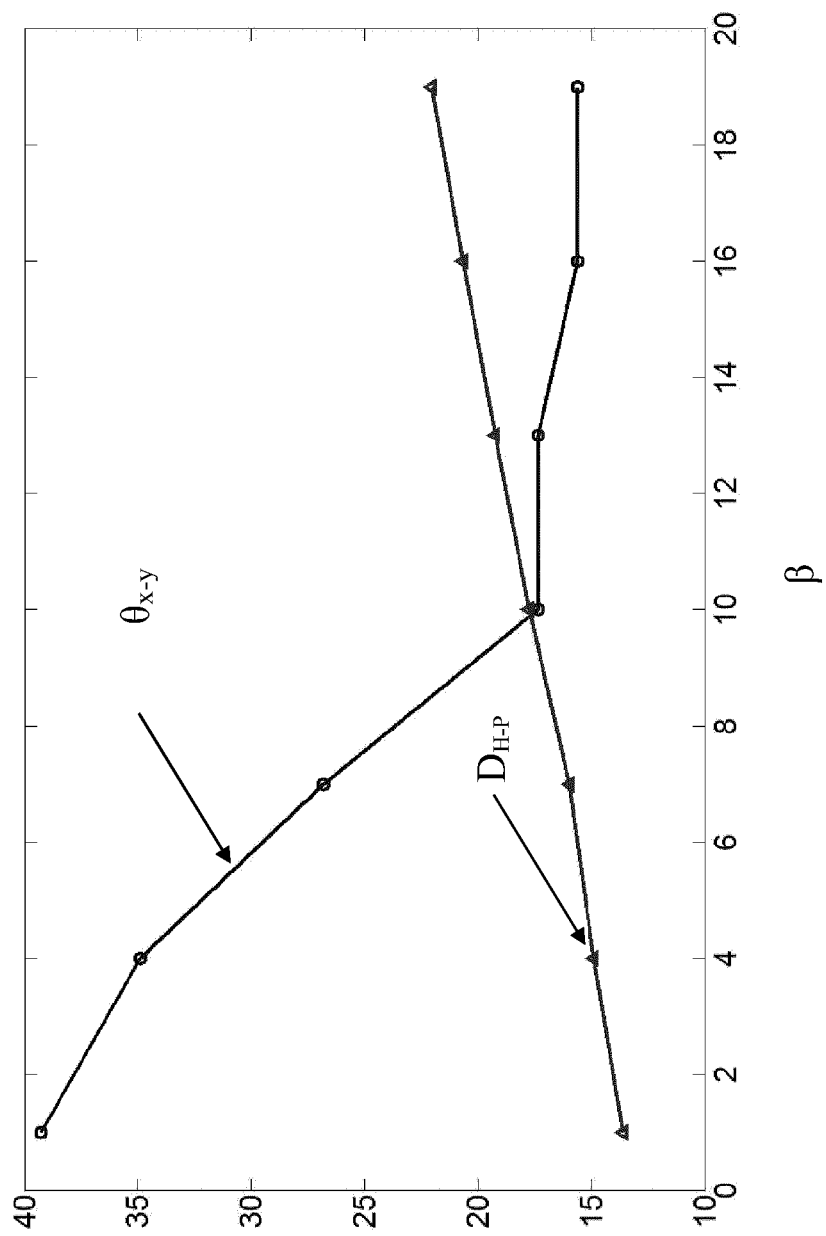
Figure 8:
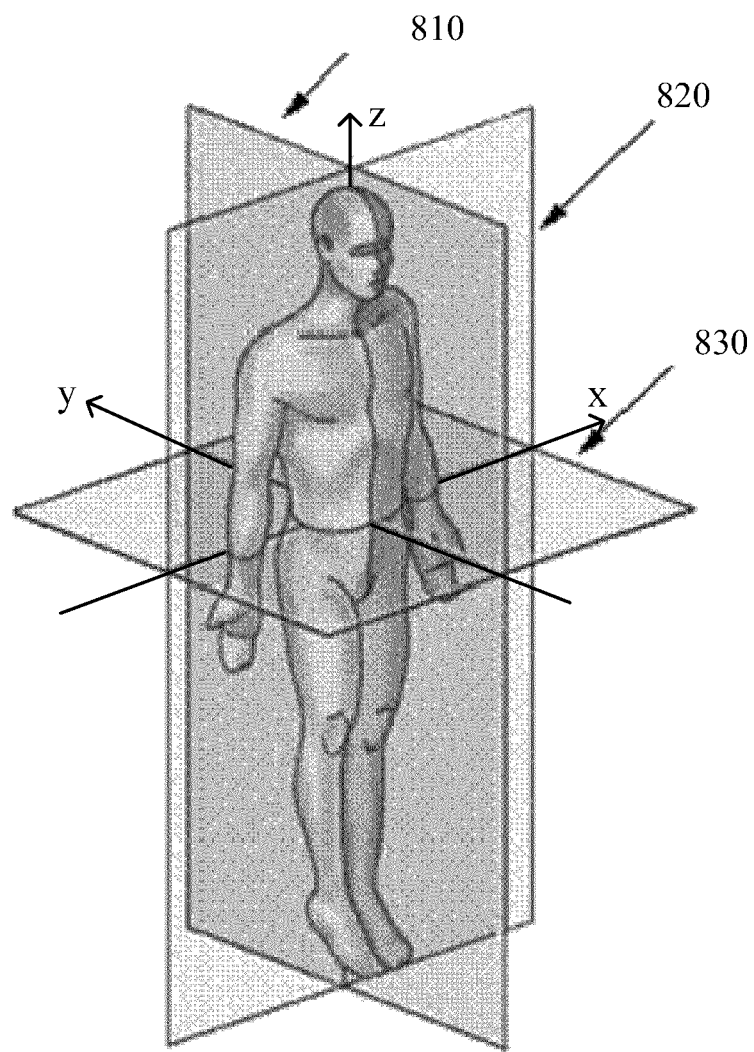

FIG. 7b illustrates the objective values of the two criteria, namely the spatial distance of the puncture trajectory and the steepness of the puncture trajectory with respect to the transverse plane (i.e. x-y plane) of the subject, achieved under different values of the weight associated with the steepness in accordance with an embodiment of the present invention; and FIG. 8 illustrates the longitudinal direction, the transverse plane, the coronal plane and the sagittal plane of a subject.

The same reference signs in the figures indicate similar or corresponding features and/or functionalities.

DETAILED DESCRIPTION OF THE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn to scale for illustrative purposes.

FIG. 8 illustrates the longitudinal direction, the transverse plane, the coronal plane and the sagittal plane of a subject.

Referring to FIG. 8, three principle planes are typically defined in human and animal anatomy:

The sagittal plane or median plane 810 (longitudinal, anteroposterior) is a plane parallel to the sagittal suture. It divides the body into left and right.

The coronal plane or frontal plane 820 (vertical) divides the body into dorsal and ventral (back and front, or posterior and anterior) portions.

The transverse plane or axial plane 830 (lateral, horizontal) divides the body into cranial and caudal (head and tail) portions.

Additionally, an x-y-z coordinate system is defined to distinguish the orientation of the planes, namely that y-axis going from front to back, the x-axis going from left to right, and the z-axis going from up to down, as illustrated in FIG. 8. The z-axis is also called the longitudinal direction.

FIG. schematically 2 illustrates an apparatus 200 for assisting a user to plan a puncture trajectory within a region-of-interest of a subject in accordance with some embodiments of the present invention.

The apparatus 200 comprises a data interface 211 configured to receive, anatomical data of the region-of-interest of the subject, and to output the at least one candidate puncture trajectory.

The anatomical data of the subject comprising three-dimensional data of the region-of-interest. In an embodiment of planning puncture trajectory for a TIPS procedure, the region-of-interest comprises the liver or a part of the liver which comprises HV branches and PV branches, and the anatomical data comprises at least three dimensional data of the HV branches and the PV branches. The data interface 211 can receive the anatomical data from one or more data sources 230 via any type of communication link. The data source 230 can be any image acquisition device such as an ultrasound probe, and/or transient or non-transient storage medium of any other information system or database.

The apparatus 200 further comprises a data processor 213 communicatively connected to the data interface 211. The data interface 211 and the data processor 213 can be an integrated unit or two separated units, and the functions of the data interface 211 and/or the data processor 213 can be provided through the use of dedicated hardware as well as hardware capable of executing software in association with appropriate software. When provided by a processor, the functions can be provided by a single dedicated processor, by a single shared processor, or by a plurality of individual processors, some of which can be shared.

The data processor 213 is configured to calculate at least one candidate puncture trajectory on basis of the anatomical data, multiple criteria, and a tradeoff among the multiple criteria.

The calculation of the at least one candidate puncture trajectory by considering multiple criteria and the tradeoff among them belongs to Multiple-criteria decision-making (MCDM) problems. Any existing way or ways developed in future for solving the MCDM problems can be applied to calculate the at least one candidate puncture trajectory. Each puncture trajectory can be represented by the coordinates of the puncture trajectory. In some embodiments where the puncture trajectory shall be a straight line, the coordinates of the puncture trajectory comprise the coordinates of the two end points of the trajectory. The multiple criteria can be of various types. Some may be defined as minimizing or maximizing certain quantity as a function of the coordinates of the trajectory, some may be defined as an upper and/or lower limit of certain quantity as a function of the coordinates of the trajectory. The tradeoff among the multiple criteria basically indicates the priorities or importance of the multiple criteria.

In some embodiments, the tradeoff among the multiple criteria can be represented by at least one weight, each weight is associated with one of the multiple criteria. A larger weight normally indicates a higher priority of the associated criteria. Additionally, the multiple criteria can be combined into a single criterion by weighting, such as by multiplying each criterion with a weight and summing up the weighted criteria. For example, the multiple criteria can be mathematically formulated as constrained, weighted cost function. Mathematically, each criterion may be associated with a weight value, but some of the weights can be fixed as predetermined values, and so the tradeoff can be represented by less number of weights then the number of the multiple criteria.

The data processor 213 is further configured, upon receiving a first user input for adjusting the tradeoff among the multiple criteria, to adjust the tradeoff among the multiple criteria on basis of the first user input, and to calculate the at least one candidate puncture trajectory on basis of the anatomical data, the multiple criteria and the adjusted tradeoff among the multiple criteria. In the embodiments where the tradeoff are represented by at least one weights, the first user input may indicate an adjustment on one or more of the at least one weights. The adjustment can be an absolute value or an increment/decrement value.

The data interface 211 is further configured to receive one or more user inputs comprising the first user input. In some embodiments, the apparatus 200 further comprises a user interface 250 for receiving the one or more user inputs. Additionally or alternatively, the apparatus 200 can be communicatively connected to a separate user interface 250. The user interface 250 can be further configured to present the at least one candidate puncture trajectory. For example, the user interface 250 can comprise a display for providing a visual presentation of the at least one candidate puncture trajectory. The display can be any device capable of providing visual presentation, such as a monitor, a projector etc. The user interface 250 can be a single device or comprises multiple devices.

The data processor is further configured to calculating at least one candidate puncture trajectory on basis of the anatomical data, the multiple criteria, and a predetermined tradeoff among the multiple criteria, and the predetermined tradeoff represents an extreme choice of the tradeoff among the multiple criteria. In some embodiments, the adjustable tradeoff are represented by one or more tradeoff parameters (such as weights) and there is a predetermined range for the adjustment of each parameters. Thus, the extreme choice of the tradeoff refers to a choice where at least one tradeoff parameter is set as the extreme value (e.g. minimal or maximal value) of the predetermined range.

The data processor 213 can be further configured to store historical data. The historical data can comprise a plurality of entries, and each entry comprises a tradeoff and the at least one candidate puncture trajectory calculated using the tradeoff. In some embodiments, the historical data can comprises each tradeoff used in previous calculations along with the at least one candidate puncture trajectory associated with each tradeoff. The used tradeoff can be predetermined tradeoff or can be a tradeoff represented by a first user input previously received. The data processor 213 is further configured to retrieve, upon a second user input for selecting a tradeoff previously used, the at least one candidate puncture trajectory associated with the selected tradeoff from the stored historical data.

Figure 1:
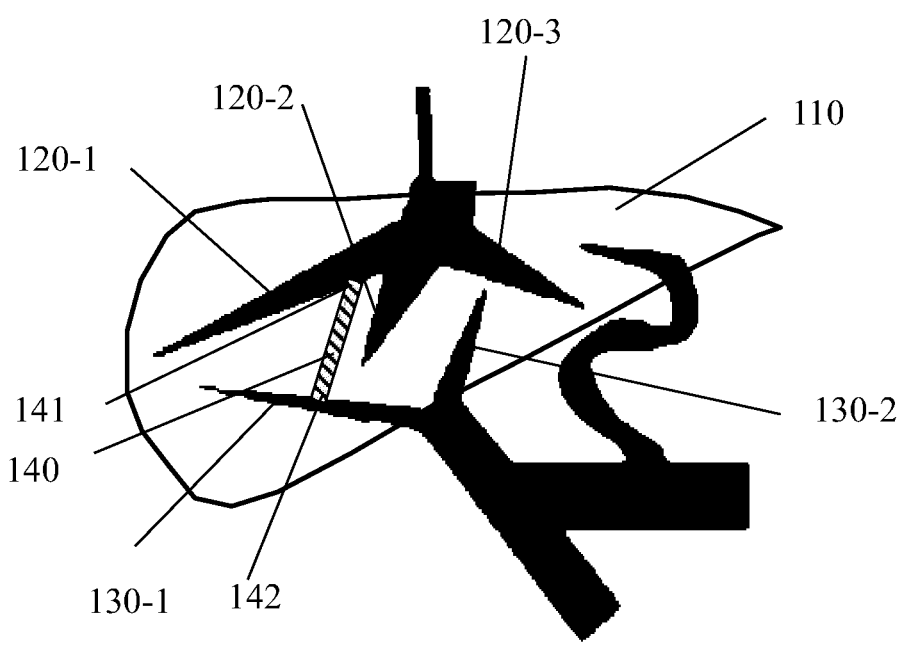
Figure 2:
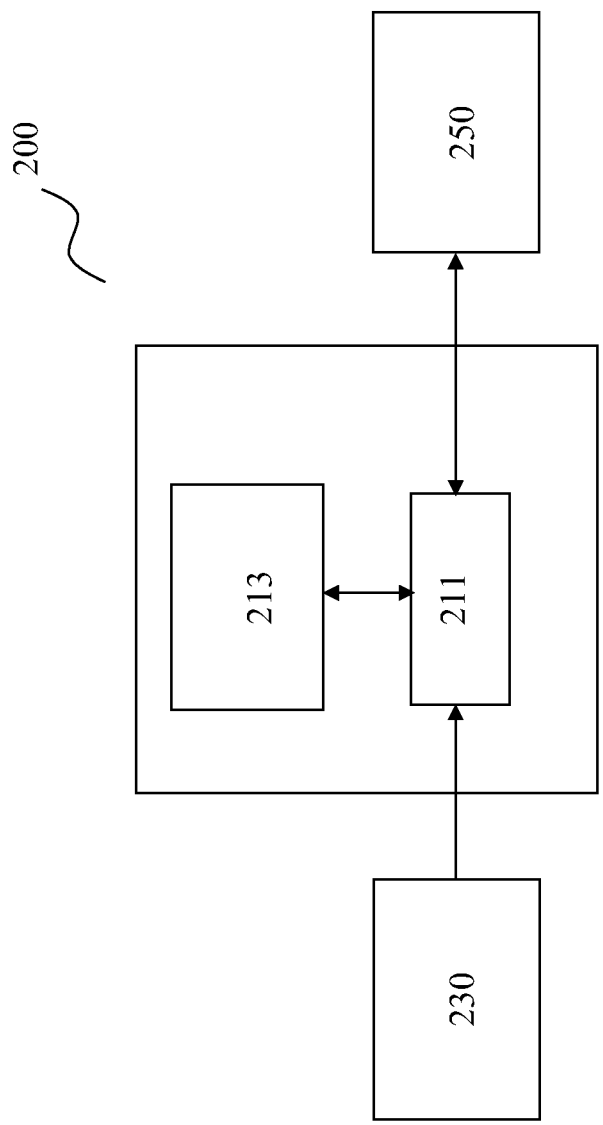
Figure 3:
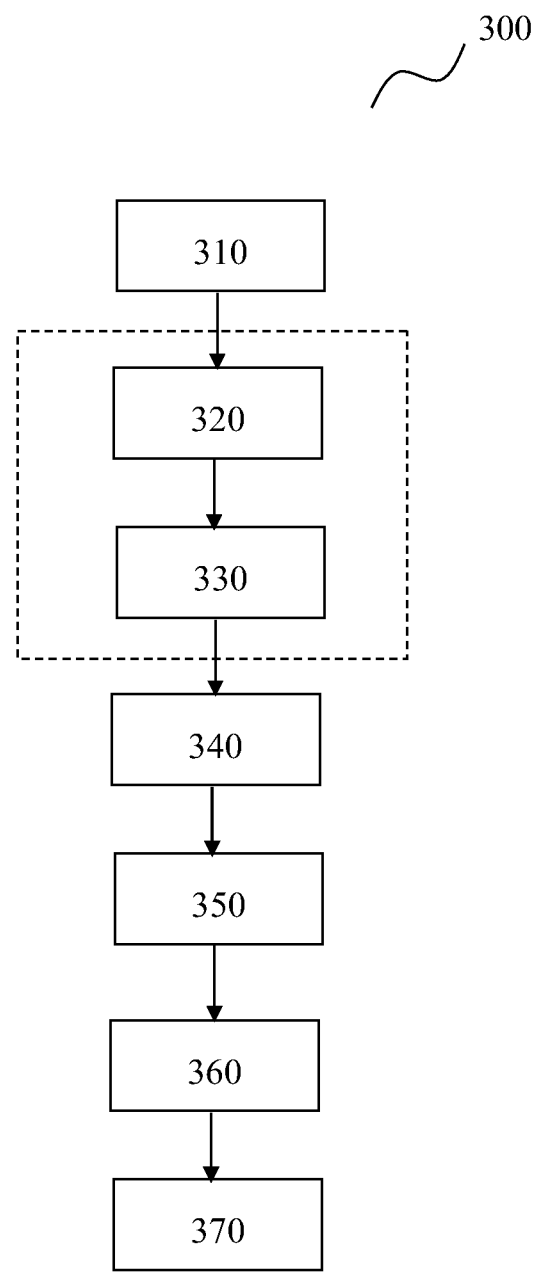

FIG. 3 schematically illustrates a method of assisting a user to plan a puncture trajectory within a region-of-interest of a subject in accordance with some embodiments of the present invention. Referring to FIG. 3, in step 310, anatomical data of the subject is received. In step 340, a first user input is received, and the first user input indicates an adjustment on the tradeoff among multiple criteria. In step 350, the tradeoff among the multiple criteria is adjusted on basis of the first user input. In step 360, the calculation of at least one candidate puncture trajectory is performed on basis of the anatomical data, the multiple criteria, and the adjusted tradeoff among the multiple criteria. In step 370, the at least one candidate puncture trajectory obtained in step 360 is output to be presented to the user. In some embodiments, between step 310 and step 340, the method further comprises steps 320 and 330. In step 320, at least one candidate puncture trajectory is calculated on basis of the anatomical data, the multiple criteria, and a predetermined tradeoff among the multiple criteria. In step 330, the at least one candidate puncture trajectory obtained in step 340 is output to be presented to the user. In some embodiments, the predetermined tradeoff represents an extreme choice of the tradeoff among the multiple criteria. Thus, the at least candidate puncture trajectory associated with the predetermined tradeoff represents the boundary cases, and the user may make use of such boundary cases to assist his/her judgement about the adjustment to the tradeoff.

Figure 4:
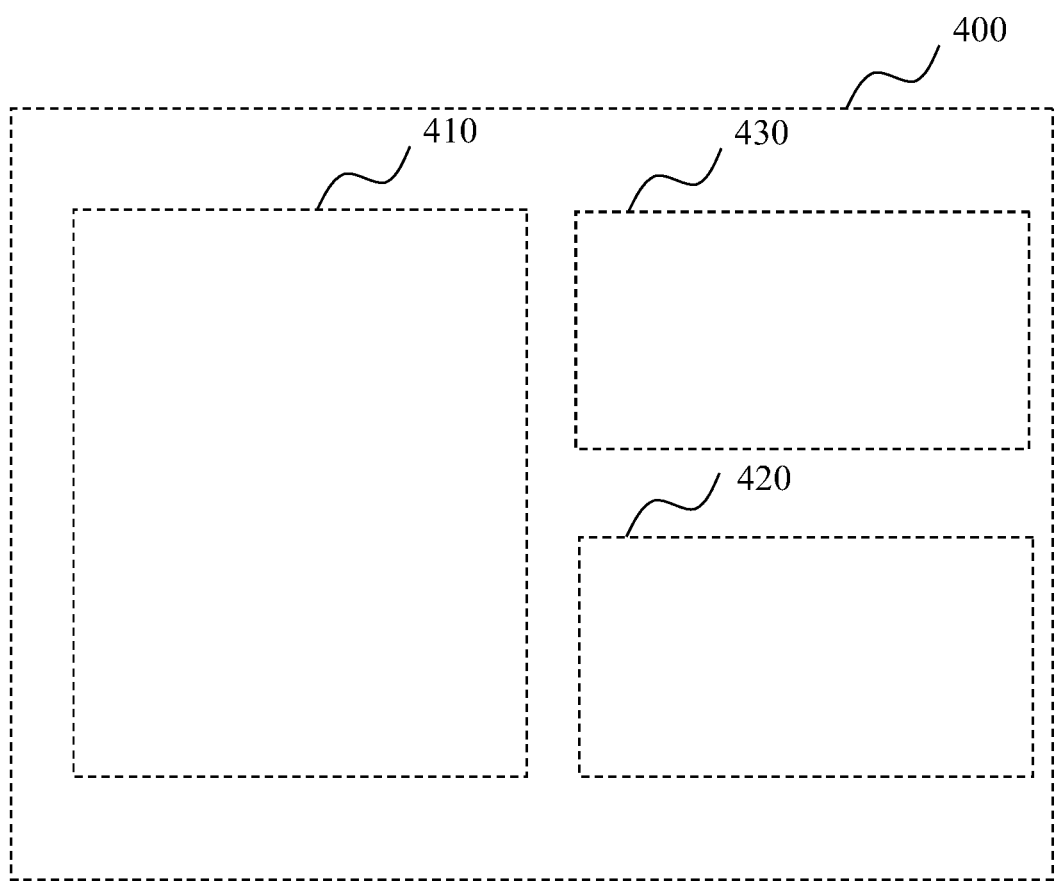

FIG. 4 schematically illustrates an exemplary view 400 presented by a user interface in accordance with some embodiments of the present invention.

As previously described, the data interface 211 is configured to output the at least one candidate puncture trajectory. In some embodiments, the data processor 213 is further configured to generate an image of the region-of-interest overlaid with the at least one candidate puncture trajectory. The image of the region-of-interest shall be interpreted in a broad sense. In some embodiments, the image of the region-of-interest can be the image of some anatomical structures extracted from the region-of-interest. For example, the image of can be the image of extracted HV branches and PV branches. Referring to FIG. 4, the view 400 can comprise a region 410 for presenting the image of the region-of-interest overlaid with the at least one candidate puncture trajectory.

In some embodiments, the data processor 213 is further configured to calculate, for each of at least one of the multiple criteria, an objective value achieved by one of the at least one candidate puncture trajectory, and the data interface 211 is configured to output the calculated objective value(s). Referring to FIG. 4, the view 400 can comprise a region 430 for presenting the objective values of one or more of the at least one candidate puncture trajectories.

Referring to FIG. 4, the view 400 can comprise a further region 420 for presenting and/or receiving the first user input. In some embodiments, the further region 420 may comprise one or more slide-like controllable bars, or one or more text input box or any other suitable input means for the user to input preferred the tradeoff. In some other embodiments, the user interface can be configured to receive the first user input in other suitable ways, such as via audio, or via gesture control, etc.

Figure 5:
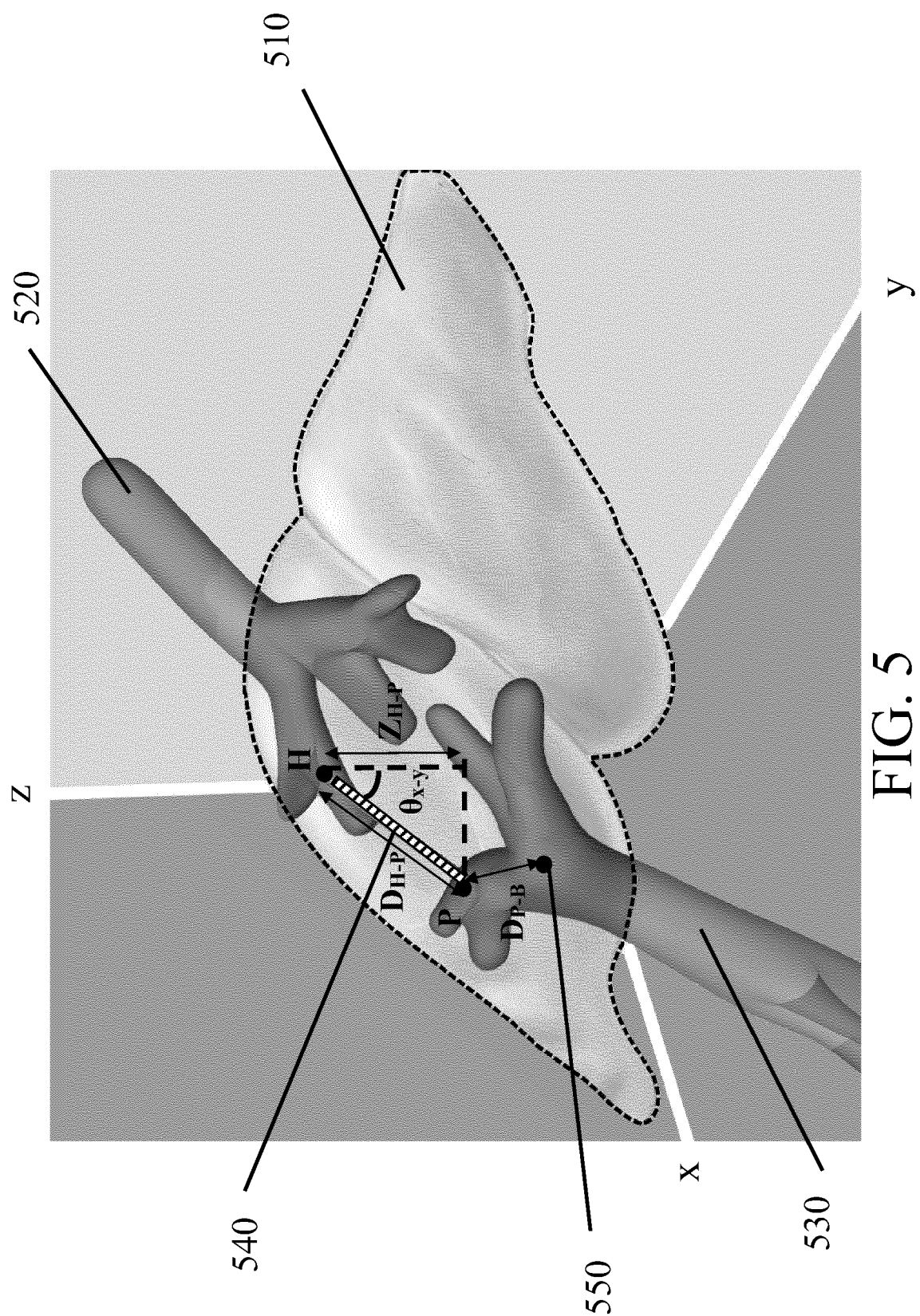

FIG. 5 schematically illustrates exemplary multiple criteria for planning a puncture trajectory for a TIPS procedure in accordance with some embodiments of the present invention. FIG. 5 illustrates a three-dimensional view of a liver region. In FIG. 5, HV 520 and PV 530 are shown to extend into the liver parenchyma 510. HV 520 comprises multiple branches. PV 530 also comprises multiple branches. A puncture trajectory for a TIPS procedure shall start from the exit point on a HV branch, advances through the liver parenchyma, and arrives at the entry point on a PV branch. A puncture trajectory 540 illustrated in FIG. 5 starts from the exit point H on a HV branch and ends at the entry point P on a HV branch. The x-y-z coordinate system in FIG. 5 is the x-y-z coordinate system defined for a subject as illustrated in FIG. 8.

In some embodiments, the multiple criteria comprises the following criteria:

Spatial distance of the puncture trajectory, denoted as $D_{H-P}$, which is regarded as a significant factor to predict the one-year shunt patency and the risk of HEP occurrence. The smaller value of $D_{H-P}$, the lower risk of shunt occlusion and HEP.

Spatial distance between bifurcation 550 of main branch of portal vein and the puncture point on the portal vein, denoted as $D_{P-B}$. It should be bigger than a predetermined threshold, such as 3 cm, to retain enough main branch of portal vein without stent invasion if the patient is to be performed with liver transplantation in the future.

Steepness of the puncture trajectory with respect to the transverse plane (i.e. x-y plane) of the subject, denoted as $\theta_{x-y}$. If the puncture trajectory is perpendicular to x-y plane, in another word, in parallel to z-axis, the steepness $\theta_{x-y}$ reaches to maximum. A large steepness value is good to avoid stent distortion, and gain better puncture visualization under DSA (Digital subtraction angiography) which essentially projects three-dimensional image into x-z plane.

Puncture slice distance along the longitudinal direction z of the subject, denoted as $Z_{H-P}$. A puncture with small $Z_{H-P}$ value may be preferred to make extra-hepatic puncture evitable.

As previously described, the multiple criteria can be formulated as a constrained, weighted cost function. In accordance with an embodiment, the calculation of the candidate puncture trajectory on basis of the above four criteria can be mathematically formulated as:

$$\min_{H,P} f(H,P) = w_1 D_{H-P} + w_2 Z_{H-P} + w_3 \theta_{x-y} \text{ such that } D_{P-B} > T$$

where $f(H, P)$ is the cost function, H represents the coordinate of the exit point of the puncture trajectory, P represents the coordinate of the entry point of the puncture trajectory, $D_{H-P}$ is the spatial distance of the puncture trajectory, $Z_{H-P}$ is the puncture slice distance, $\theta_{x-y}$ is the angle with respect to z-axis, $w_1$, $w_2$, and $w_3$ are the weights of the penalty terms of $Z_{H-P}$ and $\theta_{x-y}$, respectively, $D_{P-B}$ is the distance between the entry point and bifurcation 550 on main branch of portal vein, and T is the value constraining the minimal residual length of portal branch to keep the possibility of performing liver transplantation in the future. In some embodiments, T can be set as a value between 3 cm and 10 cm. More concretely, $D_{H-P}$, $Z_{H-P}$, and $D_{H-P}$ are calculated as:

$$D_{H-P} = \mathrm{sqrt}((Hx - Px)^2 + (Hy - Py)^2 + (Hz - Pz)^2),$$

$$Z_{H-P} = \mathrm{abs}(Hz - Pz),$$

$$\theta_{x-y} = \arccos\left(\frac{Pz - Hz}{\mathrm{sqrt}((Hx - Px)^2 + (Hy - Py)^2 + (Hz - Pz)^2)}\right)$$

where $H_x$, $H_y$ and $H_z$ are the x-y-z coordinates of the entry point H on the HV branch, and $P_x$, $P_y$ and $P_z$ are the x-y-z coordinates of the exit point P on the PV branch.

In an embodiment, the exit point H on the HV branch can be predetermined or pre-selected by the user, and then the calculation of the at least one candidate puncture trajectory can be mathematically formulated as:

$$\min_P f(P) = w_1 D_{H\text{-}P} + w_2 Z_{H\text{-}P} + w_3 \theta_{x\text{-}y}, \text{ such that } D_{P\text{-}B} > T$$

Mathematically, the above cost function would be equivalent to the following one:

$$\min_P f(P) = D_{H\text{-}P} + \alpha Z_{H\text{-}P} + \beta \theta_{x\text{-}y}, \text{ such that } D_{P\text{-}B} > T$$

That is, there are two weights $\alpha$, $\beta$ to be set. In accordance with the previously discussed strategy, the candidate puncture trajectories for boundary cases are firstly calculated by have extreme choices for the two weights, such as $\alpha=0$ and $\beta=0$, or $\alpha \gg \beta$, or $\alpha \ll \beta$, and presented to the users. Afterwards, the user may slide a value bar for each weight to adjust the weights, and see how the candidate puncture trajectories changes over the adjusted weights.

Figure 6A:
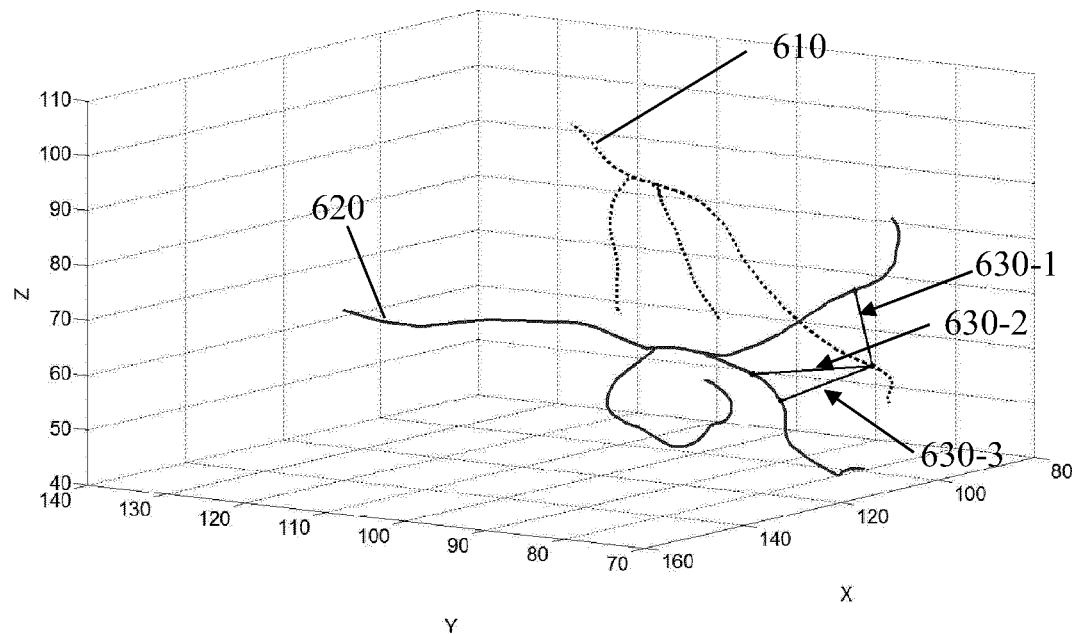
FIG. 6a illustrates a three-dimensional view of several candidate puncture trajectories overlaid with the HV branches and PV branches in accordance with an embodiment of the present invention.
Figure 6B:
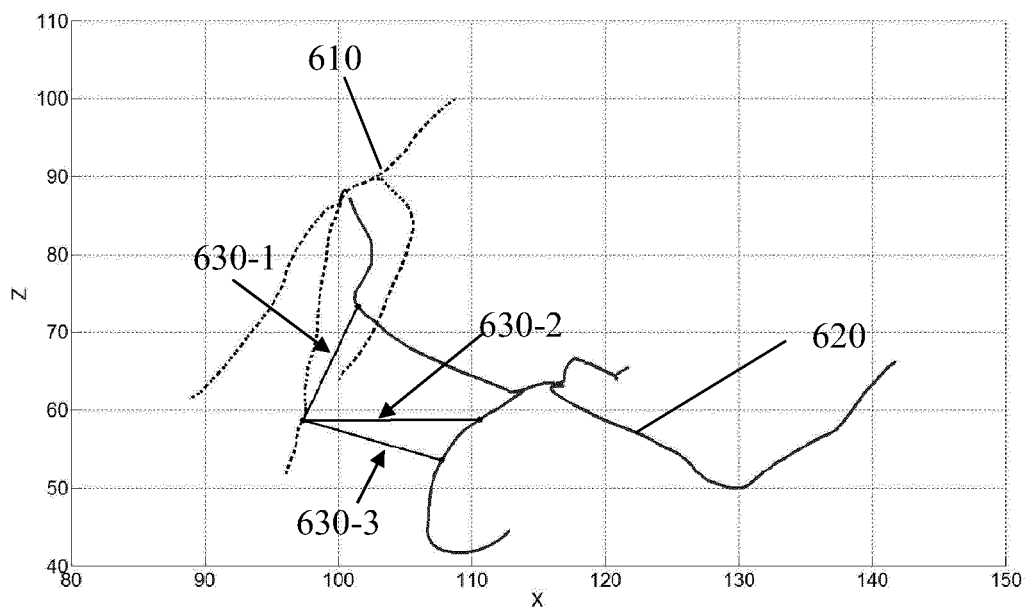
FIG. 6b illustrates a two-dimensional view obtained by projecting the several candidate punctures trajectories and the HV and PV branches of FIG. 6a onto the coronal plane (i.e. x-z plane) of the subject.

FIG. 6a illustrates a three-dimensional view of several candidate puncture trajectories 630-1, 630-2 and 630-3 (depicted in solid straight lines) overlaid with the HV branches 610 (depicted in dotted lines) and PV branches 620 (depicted in solid lines) in accordance with an embodiment of the present invention; FIG. 6b illustrates a two-dimensional view obtained by projecting the several candidate punctures trajectories and the HV and PV branches of FIG. 6a onto the coronal plane (i.e. x-z plane) of the subject. The x-y-z coordinate system in FIGS. 6a-6b is the x-y-z coordinate system defined for a subject as illustrated in FIG. 8.

In FIGS. 6a-6b, each of the candidate puncture trajectory 630-1, 630-2 and 630-3 is the solution of the following cost function under a different pair of $\alpha$ and $\beta$ values:

$$\min_P f(P) = D_{H\text{-}P} + \alpha Z_{H\text{-}P} + \beta \theta_{x\text{-}y}, \text{ such that } D_{P\text{-}B} > T,$$
where $T = 10$ cm In particular, the candidate puncture trajectory 630-3 is obtained under $\alpha=0$ and $\beta=0$. The candidate trajectory 630-3 represents the minimal puncture trajectory found over the whole branch of PV ($D_{H\text{-}P}=12.6651$ mm), while satisfying the constrained condition as will that $D_{P\text{-}B} > 10$ mm. The candidate trajectory 630-1 is the result under $\alpha=0 \ll \beta=20$, and has a spatial distance $D_{H\text{-}P}$ of 20.666 mm. The candidate trajectory 630-2 is the result under $\alpha=20 \gg \beta=0$, and has a spatial distance $D_{H\text{-}P}$ of 17.7964 mm. Although these two puncture trajectories 630-1 and 630-2 do not recommend a minimal damage of liver parenchyma, they consider the operational feasibility during intervention. Take FIG. 4b for illustration, which sets the view point on x-z plane. The trajectory 630-2 subjecting to $\alpha=20 \gg \beta=0$ gives a more horizontal line to x-axis, implying a small slices difference in z-axis, namely the value of ($H_z$-$P_z$) is small. Letting the criterion $Z_{H\text{-}P}$ associated with a much larger weight $\alpha=20$ results in the trajectory 630-2, which actually provides an intuition to IRs of what the puncture direction and PV sub-branch should be applicable to achieve a puncture access in a small slice span. Small slice span can reduce the risk of extra-hepatic puncture. The trajectory 630-1 subjecting to $\alpha=0 \ll \beta=20$ gives a more vertical line to the x-y plane, resulting in a large puncture steepness. In opposite to the trajectory 630-2, slices distance of the trajectory 630-1 is relatively big, and pinpoint the puncture direction should be toward to another PV branch. This type of puncture recommendation may more delight to some IRs as the puncture direction along spine is easy observed from DSA view. Meanwhile, the risk from stent distortion with this type of puncture tract is able to be decreased.

FIG. 7a illustrates a three-dimensional view of several candidate puncture trajectories 730-1 to 730-7 calculated under different values of weight $\beta$ associated with the steepness $\theta_{x\text{-}y}$, overlaid with the HV branches 710 and PV branches 720 in accordance with an embodiment of the present invention. The x-y-z coordinate system in FIG. 7a is the x-y-z coordinate system defined for a subject as illustrated in FIG. 8. FIG. 7b illustrates the objective values of the two criteria, namely the spatial distance $D_{H\text{-}P}$ of the puncture trajectory in unit of millimeter and the steepness $\theta_{x\text{-}y}$ of the puncture trajectory with respect to the transverse plane (i.e. x-y plane) of the subject in unit of degree, achieved under different values of the weight $\beta$ associated with the steepness $\theta_{x\text{-}y}$, in accordance with an embodiment of the present invention. In the embodiment of FIGS. 7a-7b, the weight $\alpha$ is set to be 1, and the weight $\beta$ changes from 1 to 19. The objective values illustrated in FIG. 7b are also listed in Table 1 as below.

TABLE 1 spatial distance and the steepness of the puncture trajectory under different $\beta$

| $\beta$ | 1 | 4 | 7 | 10 | 13 | 16 | 19 |
|---|---|---|---|---|---|---|---|
| $D_{H\text{-}P}$ (mm) | 13.62 | 14.89 | 15.98 | 17.74 | 19.26 | 20.67 | 22.03 |
| $\theta_{x\text{-}y}$ (degree) | 39.27 | 34.91 | 26.81 | 17.36 | 17.36 | 15.61 | 15.61 |

The three candidate puncture trajectories illustrated in FIG. 6a-6b can be regarded as an initialization to a specific entry-point. They are just the boundary cases with extreme conditions. After a rapid judgment from IRs, the IRs can change the penalty weights ($\alpha$, $\beta$ value) of cost function discretely or continuously by means of a slide-liked control bar or other suitable input means. Take $\beta$ value for instance, FIG. 7a presents the sorts of puncture recommendation in the variety of steepness value changes, in three dimensional view. FIG. 7b gives the tendency of the objective values of the two criteria $D_{H\text{-}P}$ and $\theta_{x\text{-}y}$ when $\beta$ value changes from 1 to 19. The observation from FIG. 7b is that when start point is setting on H point, the requirements of small puncture distance and steep puncture is against to each other. Under the assist of the proposed interactive approach which considers multiple criteria and provides visibility in 3D view, the IRs is in the ease of adjusting the tradeoff among the multiple criteria to determine a desirable puncture trajectory.

The technique processes described herein may be implemented by various means. For example, these techniques may be implemented in hardware, software, or a combination thereof. For a hardware implementation, the technical processes may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. With software, implementation can be through modules (e.g., procedures, functions, and so on) that perform the functions described herein. The software codes may be stored in a volatile or non-volatile storage medium and executed by the processors.

Moreover, aspects of the claimed subject matter may be implemented as a method, apparatus, system, or article of manufacture using standard programming and/or engineering techniques to produce software, firmware, hardware, or any combination thereof to control a computer or computing components to implement various aspects of the claimed subject matter. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick, key drive . . . ). Of course, those skilled in the art will recognize that many modifications may be made to this configuration without departing from the scope or spirit of what is described herein.

As used in this application, the terms "data interface", "controller", "processor" such as data processor, are intended to refer to a general-purpose processor, a specific-purpose processor, a computer processor, or a computer-related entity, either hardware, a combination of hardware and software, software, or software in execution. For example, a component may be, but is not limited to, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed among two or more computers.

What has been described above includes examples of one or more embodiments. It is, of course, not possible to describe every conceivable combination of components or methodologies for the purpose of describing the aforementioned embodiments, but one of ordinary skill in the art may recognize that many further combinations and permutations of various embodiments are possible. Accordingly, the described embodiments are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

The invention claimed is:

1. An apparatus for determination of a puncture trajectory for creating a channel between a portal vein and a hepatic vein of a subject in a medical procedure, the apparatus comprising:
a data interface configured to receive anatomical data of the subject, the anatomical data comprising three-dimensional data of a portal vein of the subject and a hepatic vein of the subject; and
a data processor configured to:
calculate at least one candidate puncture trajectory configured to create the channel between the portal vein of the subject and the hepatic vein of the subject, the data processor configured to calculate the at least one candidate puncture trajectory based on the anatomical data of the subject, multiple criteria, and a tradeoff among the multiple criteria,
wherein the multiple criteria comprises: (i) a spatial distance of the at least one candidate puncture trajectory and (ii) at least one of:
a spatial distance between a bifurcation of a main branch of the portal vein of the subject and a puncture point on the portal vein of the subject,
a steepness of the at least one candidate puncture trajectory with respect to a transverse plane of the subject, and
a puncture slice distance along a longitudinal direction of the subject; and
present, to a user, the at least one candidate puncture trajectory for determination of the puncture trajectory for use in the medical procedure.

2. The apparatus of claim 1, wherein;
the data processor is further configured, upon receiving a first user input, to;
adjust the tradeoff among the multiple criteria based on the first user input, and
calculate the at least one candidate puncture trajectory based on the anatomical data of the subject, the multiple criteria, and the adjusted tradeoff among the multiple criteria; and
the data interface is further configured to output the at least one candidate puncture trajectory.

3. The apparatus of claim 1, wherein the data processor is further configured to:
calculate at least one candidate puncture trajectory based on the anatomical data of the subject, the multiple criteria, and a predetermined tradeoff among the multiple criteria,
wherein the predetermined tradeoff represents an extreme choice of the tradeoff among the multiple criteria.

4. The apparatus of claim 2, further comprising a user interface configured to receive the first user input and to present the at least one candidate puncture trajectory.

5. The apparatus of claim 4, wherein the user interface is further configured to present the at least one candidate puncture trajectory along with the tradeoff among the multiple criteria.

6. The apparatus of claim 1, wherein the data processor is further configured to generate an image of a region-of-interest overlaid with the at least one candidate puncture trajectory.

7. The apparatus of claim 1, wherein the tradeoff among the multiple criteria is represented by at least one weight, and wherein each of the at least one weight is associated with one of the multiple criteria.

8. The apparatus of claim 1, wherein the data processor is further configured to:
store historical data comprising the calculated at least one candidate puncture trajectory associated with each first user input received, and
retrieve, upon a second user input for selecting a first user input, the at least one candidate puncture trajectory associated with the selected first user input from the stored historical data.

9. The apparatus of claim 1, wherein:
the data processor is further configured to calculate, for each of at least one of the multiple criteria, an objective value achieved by one of the at least one candidate puncture trajectory; and
the data interface is configured to output the calculated objective value.

10. The apparatus of claim 1, wherein the anatomical data comprises three-dimensional ultrasound data of the portal vein of the subject and the hepatic vein of the subject.

11. A method of determination of a puncture trajectory for creating a channel between a portal vein and a hepatic vein of a subject in a medical procedure, the method comprising:
receiving, via a data interface, anatomical data of a subject, the anatomical data of the subject comprising three-dimensional data of a portal vein of the subject and a hepatic vein of the subject;
calculating, via a data processor, at least one candidate puncture trajectory configured to create the channel between the portal vein of the subject and the hepatic vein of the subject, wherein the at least one candidate puncture trajectory is calculated based of the anatomical data, multiple criteria, and a tradeoff among the multiple criteria; and
outputting, via the data interface, the at least one candidate puncture trajectory, wherein the outputting presents, to a user, the at least one candidate puncture trajectory for determination of the puncture trajectory for use in the medical procedure,
wherein the multiple criteria comprises: (i) spatial distance of the puncture trajectory and (ii) at least one of:
a spatial distance between a bifurcation of a main branch of the portal vein of the subject and a puncture point on the portal vein of the subject;
a steepness of the at least one candidate puncture trajectory with respect to a transverse plane of the subject; and
a puncture slice distance along a longitudinal direction of the subject.

12. The method of claim 11, further comprising:
receiving a first user input; and
adjusting the tradeoff among the multiple criteria based on the first user input,
wherein the at least one candidate puncture trajectory is calculated based on the anatomical data of the subject, multiple criteria, and the adjusted tradeoff among the multiple criteria.

13. The method of claim 12, further comprising:
prior to receiving the first user input, calculating the at least one candidate puncture trajectory based on the anatomical data of the subject, the multiple criteria, and a predetermined tradeoff among the multiple criteria; and
outputting the at least one candidate puncture trajectory.

14. The method of claim 13, wherein the predetermined tradeoff represents an extreme choice of the tradeoff among the multiple criteria.

15. A computer-readable storage medium comprising instructions, which, when executed by a processor, cause the processor to;
Receive anatomical data of a subject, the anatomical data of the subject comprising three-dimensional data of a portal vein of the subject and a hepatic vein of the subject;
calculate at least one candidate puncture trajectory configured to create the channel between the portal vein of the subject and the hepatic vein of the subject, wherein the at least one candidate puncture trajectory is calculated based on the anatomical data, multiple criteria, and a tradeoff among the multiple criteria; and
output the at least one candidate puncture trajectory, wherein the output presents, to a user, the at least one candidate puncture trajectory for determination of a puncture trajectory for use in the medical procedure,
wherein the multiple criteria comprises: (i) a spatial distance of the puncture trajectory and (ii) at least one of:
a spatial distance between a bifurcation of a main branch of the portal vein of the subject and a puncture point on the portal vein of the subject;
a steepness of the at least one candidate puncture trajectory with respect to a transverse plane of the subject; and
a puncture slice distance along a longitudinal direction of the subject.

* * * * *